(12) United States Patent
Wibaux et al.

(10) Patent No.: US 9,764,059 B2
(45) Date of Patent: Sep. 19, 2017

(54) CHLORHEXIDINE GLUCONATE CONTAINING SOLVENT ADHESIVE

(71) Applicant: Avery Dennison Corporation, Glendale, CA (US)

(72) Inventors: Anne Marie Wibaux, Antwerp (BE); Vicky Van de Pol, Turnhout (BE)

(73) Assignee: Avery Dennison Corporation, Glendale, CA (US)

( * ) Notice: Subject to any disclaimer, the term of this patent is extended or adjusted under 35 U.S.C. 154(b) by 0 days.

(21) Appl. No.: 15/134,698

(22) Filed: Apr. 21, 2016

(65) Prior Publication Data

US 2016/0228600 A1    Aug. 11, 2016

Related U.S. Application Data

(62) Division of application No. 13/980,592, filed as application No. PCT/US2012/022162 on Jan. 23, 2012, now Pat. No. 9,346,981.

(60) Provisional application No. 61/434,991, filed on Jan. 21, 2011.

(51) Int. Cl.
| | | |
|---|---|---|
| *A61L 24/04* | (2006.01) | |
| *A01N 47/44* | (2006.01) | |
| *C09J 11/06* | (2006.01) | |
| *A61L 24/00* | (2006.01) | |
| *A61K 9/14* | (2006.01) | |

(52) U.S. Cl.
CPC ............ *A61L 24/043* (2013.01); *A01N 47/44* (2013.01); *A61L 24/0015* (2013.01); *C09J 11/06* (2013.01); *A61K 9/14* (2013.01); *A61L 2300/404* (2013.01)

(58) Field of Classification Search
CPC ............... A61L 24/043; A61L 24/0015; A61L 2300/404; A01N 47/44; C09J 11/06
See application file for complete search history.

(56) References Cited

U.S. PATENT DOCUMENTS

| | | | |
|---|---|---|---|
| 4,199,567 A | 4/1980 | Rankin | |
| 4,310,509 A | 1/1982 | Berglund et al. | |
| 4,434,181 A | 2/1984 | Marks, Sr. et al. | |
| 4,460,369 A | 7/1984 | Seymour | |
| 4,941,882 A | 7/1990 | Ward et al. | |
| 4,990,144 A | 2/1991 | Blott | |
| 5,270,358 A | 12/1993 | Asmus | |
| 5,322,695 A | 6/1994 | Shah et al. | |
| 5,382,451 A | 1/1995 | Johnson et al. | |
| 5,389,376 A | 2/1995 | Duan et al. | |
| 5,441,741 A | 8/1995 | Cheong | |
| 5,614,310 A | 3/1997 | Delgado et al. | |
| 5,686,096 A | 11/1997 | Khan et al. | |
| 5,717,005 A | 2/1998 | Richardson | |
| 6,455,086 B1 | 9/2002 | Trinh et al. | |
| 6,458,341 B1 | 10/2002 | Rozzi et al. | |
| 6,589,562 B1 | 7/2003 | Shefer et al. | |
| 6,599,525 B2 | 7/2003 | Scamilla Aledo et al. | |
| 6,733,745 B2 | 5/2004 | Rozzi et al. | |
| 7,704,523 B2 | 4/2010 | Serafica et al. | |
| 7,824,122 B2 | 11/2010 | Flores et al. | |
| 2002/0018814 A1 | 2/2002 | Werle et al. | |
| 2002/0072480 A1 | 6/2002 | Werle et al. | |
| 2003/0077316 A1* | 4/2003 | Nichols et al. | A61K 9/7038 424/447 |
| 2004/0170794 A1 | 9/2004 | Verhaert | |
| 2007/0116729 A1 | 5/2007 | Palepu | |
| 2010/0022654 A1 | 1/2010 | Asmus et al. | |
| 2010/0322996 A1 | 12/2010 | Wibaux et al. | |
| 2011/0067799 A1* | 3/2011 | Mussig et al. | A61L 15/58 156/94 |
| 2015/0056291 A1* | 2/2015 | Wibaux et al. | A61L 26/0066 424/492 |
| 2015/0367021 A1* | 12/2015 | Wibaux | A01N 47/44 514/635 |

FOREIGN PATENT DOCUMENTS

| | | |
|---|---|---|
| CA | 1207228 | 7/1986 |
| CA | 2333009 | 12/1999 |
| EP | 1203531 | 11/2003 |
| EP | 1784232 | 5/2007 |

(Continued)

OTHER PUBLICATIONS

Giunchedi, et al. "Formulation and in vivo evaluation of chlorhexidine buccal tablets prepared using drug-loaded chitosan microspheres," European Journal of Pharmaceutics and Biopharmaceutics, Elsevier Science Publishers B.V., Amsterdam, NL, vol. 53, No. 2, Mar. 1, 2002, pp. 233-239, XP004342819, ISSN: 0939-6411, DOI: 10.1016/S0939-6411(01)00237-5 Section 2.2 Preparation by spray-drying; table 2.
International Search Report and Written Opinion issued in corresponding IA No. PCT/US2012/022162 dated Aug. 10, 2012.
Maruzen, "New Experimental Chemistry Course 1 Basic Operation I", Sep. 20, 1975, 459-463.
Invitation to Pay Additional Fees issued in the corresponding IA No. PCT/US2012/022162 dated Apr. 12, 2012.

*Primary Examiner* — Nathan M Nutter

(74) *Attorney, Agent, or Firm* — Avery Dennison Corporation

(57) ABSTRACT

Methods for incorporating chlorhexidine salts into solvent based adhesives are described. The methods involve freeze drying an aqueous solution of the chlorhexidine salt and obtaining the chlorhexidine salt in a particulate form. The dry powder can then be dissolved into an appropriate solvent used with the adhesive of interest. Also described are particles including chlorhexidine salts that are incorporated in adhesives. Also described are various medical products utilizing the adhesive and chlorhexidine compound, and related methods of use.

20 Claims, 1 Drawing Sheet

(56) References Cited

FOREIGN PATENT DOCUMENTS

| | | |
|---|---|---|
| JP | 2002179513 | 6/2002 |
| JP | 2003534310 | 11/2003 |
| JP | 2004010545 | 1/2004 |
| JP | 2007502319 | 2/2007 |
| JP | 2014510038 | 4/2014 |
| WO | WO93/00118 | 1/1993 |
| WO | WO93/02717 | 2/1993 |
| WO | WO93/03649 | 3/1993 |
| WO | WO9900025 | 1/1999 |
| WO | WO00/36353 | 6/2000 |
| WO | 00/61692 | 10/2000 |
| WO | WO2010/080936 | 7/2010 |

* cited by examiner

CHLORHEXIDINE GLUCONATE CONTAINING SOLVENT ADHESIVE

CROSS-REFERENCE TO RELATED APPLICATION

The present application is a division of U.S. application Ser. No. 13/980,592, filed Jul. 19, 2013, which is a 371 of International Application No. PCT/US12/22162, published in English on Jul. 26, 2012, which claims the benefit of U.S. Provisional Application No. 61/434,991, filed Jan. 21, 2011, all of which are incorporated herein by reference in their entireties.

FIELD OF THE INVENTION

The present invention relates to methods for incorporating chlorhexidine salts and particularly chlorhexidine gluconate, into an adhesive; adhesives containing chlorhexidine salts; and products using such adhesive.

BACKGROUND OF THE INVENTION

A wide array of medical products use adhesive for affixing the product onto a user's skin. As will be appreciated, it is desirable to prevent or at least minimize microbial growth or reproduction along the interface of adhesive and skin, as such can readily lead to infection and other undesirable conditions.

Accordingly, artisans have incorporated a wide range of antimicrobial agents into medical products or materials. Although a limited number of such agents have been incorporated into adhesives, effective incorporation into an adhesive composition presents a formidable technical challenge for numerous other antimicrobial agents. It is difficult to efficiently disperse such agents within the adhesive. Furthermore, certain antimicrobial agents undergo a loss in efficacy upon incorporation.

Chlorhexidine gluconate has a broad antimicrobial spectrum, is safe, and is well accepted in the market. However chlorhexidine gluconate has never been incorporated into solvent based acrylic adhesives which are the standard for surgical applications due to their low cost and good adhesion on skin in dry and wet conditions.

Accordingly, it would be desirable to provide a method for incorporating chlorhexidine gluconate into an adhesive formulation such that the compound is effectively dispersed and retains its efficacy when residing in the adhesive.

SUMMARY OF THE INVENTION

The difficulties and drawbacks associated with previously known compositions, products, and practices are addressed in the present methods, adhesive compositions, products using such compositions and related methods of use.

In one aspect, the present invention provides a method of forming chlorhexidine in solid form. The method comprises providing an aqueous solution of at least one chlorhexidine salt. The method also comprises actively drying the aqueous solution to thereby obtain the at least one chlorhexidine salt in solid form.

In another aspect, the invention provides a method of forming an adhesive containing chlorhexidine. The method comprises providing an aqueous solution of at least one chlorhexidine salt and actively drying the aqueous solution to thereby obtain the at least one chlorhexidine salt in solid form. The method additionally comprises providing an adhesive component and providing a solvent compatible with the adhesive component. The method also comprises solubilizing the solid form chlorhexidine in the solvent to form a chlorhexidine solution. And, the method comprises combining the chlorhexidine solution with the adhesive component to thereby form an adhesive containing chlorhexidine.

In yet another aspect, the invention provides an adhesive formulation including chlorhexidine. The adhesive formulation comprises an adhesive, and at least one chlorhexidine salt.

In still another aspect, the present invention provides a medical product having an adhesive with antimicrobial properties. The medical product comprises an adhesive formulation including chlorhexidine.

As will be realized, the invention is capable of other and different embodiments and its several details are capable of modifications in various respects, all without departing from the invention. Accordingly, the description is to be regarded as illustrative and not restrictive.

DETAILED DESCRIPTION OF THE EMBODIMENTS

Figure 1:
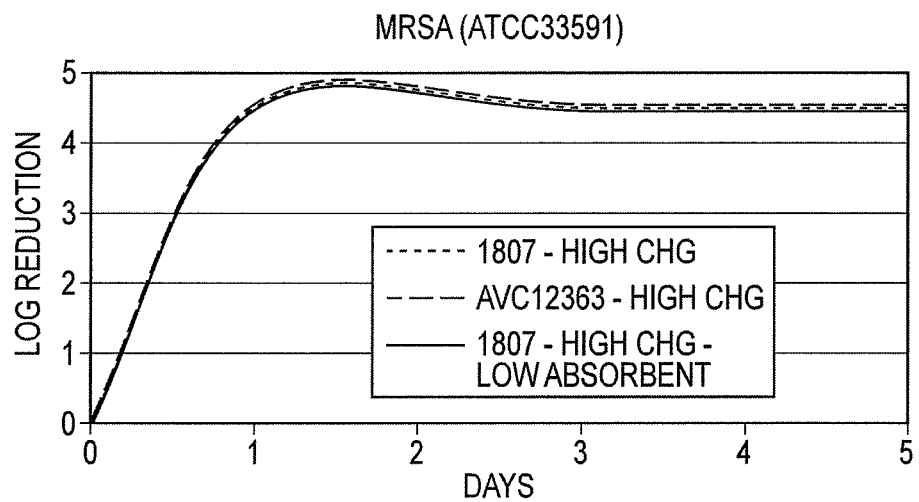
FIG. 1 is a graph illustrating antimicrobial efficacy of various adhesive samples described herein.

It is believed that the inclusion of chlorhexidine gluconate (CHG) into solvent based adhesives has not been achieved yet due to certain physical and chemical properties of chlorhexidine gluconate. For example, chlorhexidine gluconate is strongly hydrophilic and is only soluble in methanol and acetone. In addition, chlorhexidine gluconate is typically commercially available as a 20% or 40% by weight in water formulation. Aqueous compositions can not be readily combined with solvent based adhesives. Chlorhexidine gluconate is sensitive to high temperatures thereby limiting its subsequent processing as would otherwise likely be necessary in any adhesive incorporation. And, when dried by evaporation, the compound does not readily disperse in solvent. This presents another difficulty in attempting to incorporate this compound into a solvent based adhesive.

The present invention provides a unique strategy for incorporating chlorhexidine gluconate into a solvent based adhesive such as solvent based acrylic adhesives which are widely used in medical and surgical applications. The new method incorporates chlorhexidine gluconate into a solvent based adhesive by an active drying operation and preferably by freeze drying or spray drying, chlorhexidine gluconate to obtain a powder. The powder is then dissolved in a solvent that is compatible with the adhesive of interest such as an acrylic adhesive. An example of a suitable solvent for a typical acrylic adhesive is methanol.

Chlorhexidine

Chlorhexidine is a chemical antiseptic and generally used as an antimicrobial agent. It is effective on both Gram-positive and Gram-negative bacteria, although it is less effective with some Gram-negative bacteria. It has both bactericidal as well as bacteriostatic mechanisms of action, the mechanism of action being membrane disruption and not ATPase inactivation as previously thought. It is also useful against fungi and enveloped viruses, though this has not been extensively investigated. Products containing chlorhexidine in high concentrations should be kept away from eyes and the ears, due to the risk of damage to those organs. However, chlorhexidine is safely used in very low concentrations, for example in some contact lens solutions.

Chlorhexidine gluconate (also known as chlorhexidine digluconate) is a salt of chlorhexidine and gluconic acid. The structural formula of chlorhexidine gluconate is:

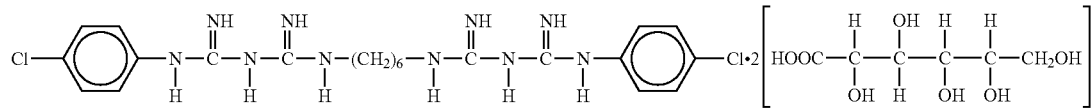

Although this compound is actually a digluconate compound, it is commonly referred to as chlorhexidine gluconate.

Thus, the term chlorhexidine gluconate as used herein encompasses the digluconate compound. Also, the terms "chlorhexidine gluconate" and "chlorhexidine digluconate" are used interchangeably herein.

Pharmaceutically acceptable chlorhexidine salts that may be used as antimicrobial agents according to the invention include, but are not limited to, chlorhexidine palmitate, chlorhexidine diphosphanilate, chlorhexidine dihydrochloride, chlorhexidine diacetate, and chlorhexidine digluconate. Chlorhexidine free base is a further example of an antimicrobial agent.

Thus, the present invention provides methods for incorporating one or more chlorhexidine salts and particularly chlorhexidine gluconate in a solvent based adhesive such as an acrylic adhesive. Although the present invention is particularly directed to the incorporation of chlorhexidine gluconate, the invention is applicable to other chlorhexidine salts and related compounds. Generally, any chlorhexidine salt that is generally provided or produced in an aqueous or liquid form is a candidate for the various preferred aspects of the invention as described herein.

Active Drying

Water and/or any other solvents or liquids are removed and separated from the chlorhexidine salt(s) by one or more active drying operations. The term "active drying" refers to any operation in which liquid and typically water, is removed and separated from the chlorhexidine salt(s) besides passive evaporation of the liquid. Passive evaporation refers to evaporation of the liquid component(s) at ambient temperatures without any moving air streams or other flowing currents to aid in removal and separation of the liquid component(s) from the chlorhexidine salt(s).

Thus, the term active drying as used herein refers to a wide array of liquid removal techniques such as but not limited to aggressive evaporation using airflows over the liquid also known as pneumatic drying, heating promoted evaporation in which thermal energy is supplied to the liquid also known as hot air drying, drying by exposure to electromagnetic radiation such as microwave energy, freeze drying, and spray drying for example. Combinations of these and other drying strategies can be utilized. Preferably, active drying is performed by freeze drying or spray drying.

Freeze drying is a dehydration process typically used to preserve a perishable material or render the material more convenient for transport. Freeze drying is typically performed by freezing the material and then reducing the surrounding pressure and adding sufficient heat to allow the frozen water in the material to sublime directly from the solid phase to the gas phase.

A preferred method in accordance with the present invention is to freeze dry a 20% (all percentages are percentages by weight unless noted otherwise) chlorhexidine gluconate solution. Freeze drying may be performed in nearly any manner. In one embodiment of the invention, the noted solution of 20% chlorhexidine gluconate and 80% water is fully frozen by subjecting the solution to a temperature of about -20° C. and a pressure of about 0.180 bars, for a time period of about 24 hours. It will be appreciated that these temperature, pressure, and time values are merely representative. The invention includes a significantly broader range of freeze drying conditions. Typically, temperatures are within a range of from about -80° C. (or less) to about 10° C. (or more), and preferably from about -50° C. to about 0° C. Typically, pressures are within a range of from about 0.01 bars to about 0.95 bars, and preferably from about 0.10 bars to about 0.50 bars. Typical time periods range from several seconds up to several days.

The aqueous chlorhexidine gluconate solution is preferably placed in a vessel that increases the surface area of the solution. As will be appreciated, increasing the solution surface area promotes heat transfer and thus reduces the time period necessary to freeze the aqueous chlorhexidine gluconate solution. Increasing the surface area also promotes migration and sublimation of water from the frozen mass to thereby leave a remaining component of chlorhexidine gluconate.

Although the preferred methods described herein utilize a 20% chlorhexidine gluconate solution which is then freeze dried, it will be understood that the invention is not limited to such. As previously noted, chlorhexidine gluconate is also typically available as a 40% aqueous solution and so such may be freeze dried as described herein. It is contemplated that a range of aqueous solutions having concentrations of from about 1% up to the solubility limit of the compound could be used. Typically for many chlorhexidine salts, they are commercially available in an aqueous solution and in a concentration of from about 1% to about 60%.

During freeze drying, after initially freezing the aqueous solution to form a solid, at least a portion of the water is removed from the solid by sublimation. The present invention includes operations in which the water component is partially removed by other techniques or practices besides freeze drying. However, preferably at least a majority and most preferably all of the water is removed via freeze drying.

Another preferred active drying technique is spray drying. Spray drying is a method of producing a dry powder from a liquid or slurry by rapidly drying with a hot gas. This is the preferred method of drying of many thermally sensitive materials such as foods and pharmaceuticals. A consistent particle size distribution is a reason for spray drying some industrial products such as catalysts. Air is typically the heated drying media. However, if the liquid is a flammable solvent or the product is oxygen-sensitive then nitrogen can be used.

All spray dryers use some type of atomizer or spray nozzle to disperse the liquid or slurry into a controlled drop size spray. The most common of these are rotary nozzles and single fluid pressure swirl nozzles. Alternatively, for some applications two-fluid or ultrasonic nozzles are used. Depending on the process requirements, drop sizes from 10 to 500 micrometers can be achieved with the appropriate nozzle selection. The most common drop sizes are in the 100 to 200 micrometer diameter range. The resulting dry powder is often free-flowing.

The hot drying gas can be passed as a co-current or counter-current flow to the atomizer direction. A co-current flow enables the particles to have a lower residence time within the system and the particle separator (typically a cyclone device) operates more efficiently. The counter-current flow method enables a greater residence time of the particles in the chamber and usually is paired with a fluidized bed system.

Additional techniques and/or alternative active drying operations can include for example combinations of spray drying and freeze drying.

Incorporation of Chlorhexidine in Adhesive

After forming a powder of chlorhexidine gluconate or other chlorhexidine salt by one or more active drying operations optionally including one or more size reducing operations, the powder can be readily solubilized by adding the chlorhexidine gluconate in particulate form to one or more suitable solvent(s) such as methanol. The chlorhexidine gluconate is added to the solvent in an amount such that the compound readily dissolves in the solvent. For using methanol as the solvent, a concentration of chlorhexidine gluconate in a range from about 15% to about 20% has been found acceptable. However, it will be appreciated that the invention includes the use of concentrations greater than and less than these values.

After dissolving the chlorhexidine gluconate powder (or other salt of chlorhexidine) into a suitable solvent, the chlorhexidine gluconate solution is incorporated into a solvent based adhesive. Typically, this is performed by adding or otherwise incorporating the solution directly into an adhesive component or adhesive formulation.

The adhesive containing chlorhexidine salt is then incorporated in a product or used as desired. For example, conventional coating and drying operations can be performed to form an adhesive layer on a medical product. Representative non-limiting examples of such medical products include surgical goods such as incise films, and device fixation products; wound care products; and ostomy pouches.

In certain embodiments, the adhesive can be covered with a carrier, preferably a polyurethane film or any alternative material.

Adhesives

The methods of the invention can be used to incorporate chlorhexidine salts such as chlorhexidine gluconate, into a wide array of adhesives, and preferably a solvent based adhesive. Non limiting adhesives include acrylic adhesives, rubber adhesives, silicone adhesives, polyurethane adhesives, and variants and combinations thereof. Generally, the resulting chlorhexidine salt which is preferably chlorhexidine gluconate, can be incorporated into nearly any non-aqueous based adhesive. Preferably, the adhesive is a solvent based adhesive. More preferably, the adhesive is a solvent based acrylic adhesive.

The present invention also includes combining chlorhexidine powder produced by the methods described herein, with an adhesive component such as an adhesive ingredient and/or an adhesive premix. This strategy provides an alternative approach for subsequent formation of a chlorhexidine containing adhesive.

It is also contemplated that one or more chlorhexidine salts can be incorporated into an adhesive by combining a liquid solution, mixture or dispersion containing chlorhexidine salt(s) into an adhesive formulation or an adhesive intermediate and then subjecting the resulting mixture to one or more drying operations to thereby remove the liquid component(s) from the mixture of adhesive and chlorhexidine salt(s).

For embodiments in which the chlorhexidine is in a particle form, another advantage results when the particles are incorporated into a hydrophobic adhesive matrix. Due to its hydrophilic properties, chlorhexidine and particularly chlorhexidine gluconate, will easily release from a hydrophobic adhesive matrix.

Additional Additives

One or more additional additives can be incorporated into the adhesive and chlorhexidine formulation. Preferably the additional additives include medicinal compounds. Such medicinal compounds include, but are not limited to, antimicrobials, antibiotics, antifungal agents, antiviral agents, antithrombogenic agents, anesthetics, anti-inflammatory agents, analgesics, anticancer agents, vasodilation substances, wound healing agents, angiogenic agents, angiostatic agents, immune boosting agents, growth factors, and other biological agents. Suitable antimicrobial agents include, but are not limited to, biguanide compounds; triclosan; penicillins; tetracyclines; aminoglycosides, such as gentamicin and Tobramycin™; polymyxins; rifampicins; bacitracins; erythromycins; vancomycins; neomycins; chloramphenicols; miconazole; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds provide for enhanced antimicrobial activity.

In certain applications, the adhesive composition may comprise one or more absorbents. An example of a suitable absorbent is a hydrocolloid agent. The hydrocolloid may be linear or crosslinked. Suitable hydrocolloids include synthetic hydrocolloids such as sodium carboxymethyl cellulose, and natural products such as gelatin, pectin, guar gum, locust bean gum, tragacanth gum, gum karaya, starches, gum arabic, alginic acid and its sodium and/or calcium salts. Other synthetic hydrocolloids such as polyvinyl alcohol, polyvinyl acetate, polyvinyl pyrollidone, polyacrylic acid, polyhydroxyalkyl acrylates, polyacrylamides, high molecular weight polyethylene glycols and polypropylene glycols are useful. Others hydrocolloids include crosslinked or crystalline sodium carboxymethyl cellulose, crosslinked dextran and starch-acrylonitrile graft copolymer.

EXAMPLES

A series of trials were conducted to evaluate adhesives containing chlorhexidine agents, their processability, and antimicrobial efficacy of the resulting compositions. The adhesive compositions included an adhesive component, an absorbent agent, and an antimicrobial agent.

A listing of the raw materials is set forth below in Table 1.

TABLE 1

| Raw Materials | | |
|---|---|---|
| Component | Designation | Source |
| Adhesive | I807 | Avery Dennison |
| | AVC-12363 | Avery Dennison |

TABLE 1-continued Raw Materials

| Component | Designation | Source |
|---|---|---|
| Absorbent | A800 (carboxymethyl cellulose) | Aqualon |
| Antimicrobial | CHG USP/EurPh | Medichem |
| Liner | BG684 | Avery Dennison |
| Carrier | Med5575A | Avery Dennison |

The 1807 adhesive is an acrylic adhesive commercially available from Avery Dennison. The AVC-12363 adhesive is also available from Avery Dennison and is a solvent acrylic adhesive suitable for medical applications such as for adhesive dressings, securement devices, incise films, etc.

Samples of the composition were prepared as follows. 20% chlorhexidine water based solution was freeze dried. Wet adhesive was weighted and added into a breaker. A800 carboxymethyl cellulose (particle size less than 75 µm) was added directly into the adhesive under mixing at 800 rpm.

The freeze dried chlorhexidine gluconate powder was dissolved in methanol at a concentration of 15%. The chlorhexidine gluconate solution was then added into the adhesive under mixing at 800 rpm.

The adhesive containing the carboxymethyl cellulose and chlorhexidine gluconate stayed under mixing for 30 minutes at 800 rpm.

Adhesives were then coated at 100 gsm onto a BG684 release liner. Coating speed used was 4 m/min.

Coatings were dried in an oven at 95° C. for 15 minutes.

Med5575A was manually laminated on top of the coating as carrier.

The following test methods were used at evaluate multilayer prototypes as noted in Table 2 as follows:

TABLE 2

Test Methods

| Test | Standard |
|---|---|
| 90° Peel PE | T04/095 |
| Tack | T04/001 |
| Water Vapor Transmission | T06/022 |
| Static Absorption | T06/022 |
| Fluid Handling Capacity (FHC) | T06/022 |
| Antimicrobial Efficacy | ASTM2180 |

Regarding the test procedures, the T06/022 procedure corresponds to EN13726. Details as to T04/001 and T04/095 are as follows:

T04/001—Finat Tack onto Glass

Definition: The tack property of a pressure sensitive material is the force required to separate a loop of material which has been brought into contact with a specified area of a standard surface instantly (or substantially so), using no external pressure to secure more thorough contact.

Significance: Tack is a measure of a tape's ability to adhere instantly with a minimum of pressure.

Test specimen: The test specimens had a width of 25 mm and a length of 150 mm. The test specimen was cut with a suitable cutter, normally in the machine direction.

Equipment: A flat "Float Process" glass plate with a minimum thickness of 3.0 mm was used. A metal peg was attached at the center of the plate. The dimensions of the peg should be such that the peg can be clamped in the lower jaw of an adhesion tester. 37 micron polyester film is used.

Test method: Prior to testing, the glass panels were cleaned. To determine the tack, the side of the glass not to be tested was covered with 37 micron polyester film. The test strips were 25 mm wide and 150 mm long. The cuts should be clean and straight. The backing paper from each strip was removed immediately prior to the test being carried out. The test samples were positioned as follows. The two ends of the sample were held and formed into a loop, with the adhesive surface directed outward, by bringing the two ends together. The free ends were covered with polyester to protect the jaws of the adhesion tester from the adhesive coating. The polyester-protected ends of the sample were placed in between the jaws in such a way that a loop of 150 mm was formed. The tester was started and the loop was brought into contact with the glass plate at a speed of 300 mm per minute. When full contact over the glass plate was achieved (25×25 mm), the direction of the tester was immediately reversed thereby allowing separation to take place at a speed of 300 mm per minute. It is important that delay in reversing direction is kept to a minimum. The maximum force necessary to separate the loop completely from the glass plate was recorded.

Report: The tack report includes the tack value in Newton per meter width (N/m). If other than 25 mm widths are tested, Newton per meter values are obtained by dividing the observed value by the width of the specimen. Report which side of the tape the values represent (laminating or mounting), and if the value is obtained from a deviating test width, then this specific width should also be mentioned. The rigidity of the specimen affects the results and must be considered when comparing different adhesives on different carriers. Report the tack value in Newton per meter width (N/m).

T04/095—90° Peel Adhesion onto Mattflex Polyethylene in CD (4.5 pounds, 20 minutes dwell), Used for all Products Coated with Acrylic Adhesives Definition: Peel adhesion onto polyethylene is the force (average) required to remove a pressure sensitive tape from a test panel at a specified angle and speed using a defined pressure to establish contact.

Equipment: The following equipment was used for this evaluation:
Adhesion Tester
Aluminum panel (15 cm×15 cm)
DC tape
2050 g roller (4.5 pound) ASTM D1000
Polyethylene foil (25 µm) (standard PE testing side is typically an interior face of the roll)
Supplier ACE
Ref 7660 Female side pre-treated
Paper strip 25×230 mm
Paper (no lacquering)

Preparation of Samples: Test material and polyethylene test substrates were conditioned for 24 hours at a temperature of 23±2° C. and at a relative humidity at that temperature of 50±2%. A DC-tape was laminated onto the aluminum panel. The untreated side of the polyethylene foil was laminated onto the self-adhesive aluminum panel with a hard rubber roller. The polyethylene foil was protected with a clean unlacquered paper. The test specimens had a width of 25 mm and a length of approximately 150 mm. The test specimens were cut with a suitable cutter, in the machine direction. At the edge a paper strip was laminated with overlapping of ±1 cm.

Measurement: The liner of test specimen was removed and the test specimen was laminated in cross direction onto the polyethylene foil. The sample was rolled with the ASTM roller with a constant speed of 150 cm/min. After waiting for 20 minutes, measurement with the adhesion tester was started. The end of the paper strip was clamped in the upper grip and the aluminum panel was clamped in the lower grip.

The test angle between paper strip and the aluminum panel was 90°.

Reporting: 90° peel is the averaged force required to remove the test specimen from the test substrate (N/25 mm).

Prototypes were prepared based on two adhesives. 1807 was chosen for its well known application in negative pressure wound therapy (NPWT) (long term application on skin). AVC12363 was selected for its polymer structure. AVC-12363 does not contain any —COOH functional groups.

Tables 3 and 4 summarize the performance and characteristics of multilayer assemblies formed using the adhesive compositions described herein. The designation "FD CHG" in the column "Antimicrobial" refers to freeze dried chlorhexidine gluconate as described herein. The term "AMX" refers to antimicrobial efficacy. The term "PAPE" refers to adhesion on polyethylene. The term "FHC" refers to fluid handling capacity. And, the reference "NT" refers to not nested.

TABLE 3

Multilayer Assemblies Using I807 Adhesive

| Sample ID | Coat Weight (g/m²) | Adhesive | % A800 (w/w) | Antimicrobial | AMX Concentration % (w/w) | PAPE T04/095 (N/25 mm) | Tack T04/001 (N/25 mm) | FHC T06/022 (g/m²/24 h) | Static Absorption T06/022 (g/m²/24 h) | MVTR T06/022 (g/m²/24 h) |
|---|---|---|---|---|---|---|---|---|---|---|
| 1 | 85 | I807 | 0 | FD CHG | 9 | 2.75 | 18.0 | NT | NT | 324 |
| 2 | 85 | I807 | 0 | FD CHG | 9 | 3.36 | 18.1 | NT | NT | 334 |
| 3 | 85 | I807 | 0 | FD CHG | 9 | 2.95 | 17.6 | NT | NT | 347 |
| 4 | 96 | I807 | 0 | FD CHG | 3 | 3.50 | 26.8 | NT | NT | 315 |
| 5 | 96 | I807 | 0 | FD CHG | 3 | 3.61 | 26.0 | NT | NT | 327 |
| 6 | 96 | I807 | 0 | FD CHG | 3 | 3.56 | 26.1 | NT | NT | 330 |
| 7 | 96 | I807 | 0 | None | 0 | 3.59 | 30.5 | NT | NT | 308 |
| 8 | 96 | I807 | 0 | None | 0 | 3.28 | 32.7 | NT | NT | 321 |
| 9 | 96 | I807 | 0 | None | 0 | 3.79 | 33.3 | NT | NT | 306 |
| 10 | 100 | I807 | 20 | FD CHG | 9 | 1.44 | 0.5 | 2090 | 1400 | 690 |
| 11 | 100 | I807 | 20 | FD CHG | 9 | 1.50 | 1.7 | 2290 | 1600 | 690 |
| 12 | 100 | I807 | 20 | FD CHG | 9 | 1.57 | 0.9 | 2820 | 2110 | 710 |
| 13 | 92 | I807 | 20 | None | 0 | 1.45 | / | 2320 | 1160 | 1160 |
| 14 | 92 | I807 | 20 | None | 0 | 1.48 | 12.7 | 2310 | 1140 | 1170 |
| 15 | 92 | I807 | 20 | None | 0 | 1.19 | 13.7 | 2160 | 1040 | 1120 |
| 16 | 110 | I807 | 40 | FD CHG | 3 | 0.62 | 0.7 | 3480 | 2800 | 680 |
| 17 | 110 | I807 | 40 | FD CHG | 3 | 0.93 | 1.2 | 3150 | 2460 | 680 |
| 18 | 110 | I807 | 40 | FD CHG | 3 | 0.63 | 0.6 | 3380 | 2550 | 830 |
| 19 | 106 | I807 | 20 | FD CHG | 5 | 1.65 | 7.6 | 1640 | 900 | 740 |
| 20 | 106 | I807 | 20 | FD CHG | 5 | 2.93 | 7.9 | 1850 | 1080 | 770 |
| 21 | 106 | I807 | 20 | FD CHG | 5 | 1.86 | 10.1 | 1810 | 990 | 820 |
| 22 | 105 | I807 | 20 | FD CHG | 3 | 2.16 | 13.5 | 1710 | 1040 | 670 |
| 23 | 105 | I807 | 20 | FD CHG | 3 | 1.96 | 12.5 | 1510 | 870 | 640 |
| 24 | 105 | I807 | 20 | FD CHG | 3 | 1.63 | 10.9 | 1690 | 950 | 740 |
| 25 | 116 | I807 | 40 | FD CHG | 5 | 0.85 | 0.1 | 1470 | 750 | 720 |
| 26 | 116 | I807 | 40 | FD CHG | 5 | 0.65 | 0.1 | 1550 | 840 | 710 |
| 27 | 116 | I807 | 40 | FD CHG | 5 | 0.61 | 0.2 | 1740 | 840 | 900 |
| 28 | 112 | I807 | 30 | FD CHG | 3 | 1.27 | 4.6 | 2130 | 1470 | 660 |
| 29 | 112 | I807 | 30 | FD CHG | 3 | 8.85 | 4.0 | 2270 | 1590 | 680 |
| 30 | 112 | I807 | 30 | FD CHG | 3 | 1.53 | 5.6 | 2260 | 1500 | 760 |
| 31 | 112 | I807 | 20 | None | 0 | 1.94 | 17.5 | 1900 | 1300 | 600 |
| 32 | 112 | I807 | 20 | None | 0 | 2.07 | 15.8 | 1860 | 1300 | 530 |
| 33 | 112 | I807 | 20 | None | 0 | 1.88 | 14.3 | 2030 | 1320 | 710 |
| 34 | 104 | I807 | 30 | FD CHG | 5 | 1.10 | 1.3 | 2710 | 2100 | 610 |
| 35 | 104 | I807 | 30 | FD CHG | 5 | 1.25 | 2.2 | 2630 | 1990 | 640 |
| 36 | 104 | I807 | 30 | FD CHG | 5 | 0.78 | 3.0 | 2690 | 1970 | 720 |
| 37 | 73 | I807 | 0 | FD CHG | 5 | 3.03 | 20.0 | 590 | 160 | 430 |
| 38 | 73 | I807 | 0 | FD CHG | 5 | 2.93 | 16.2 | 590 | 80 | 450 |
| 39 | 73 | I807 | 0 | FD CHG | 5 | 2.91 | 14.8 | 510 | 80 | 430 |
| 40 | 84 | I807 | 0 | FD CHG | 3 | 3.77 | 20.5 | 420 | 80 | 340 |
| 41 | 84 | I807 | 0 | FD CHG | 3 | 2.92 | 21.8 | 490 | 110 | 380 |
| 42 | 84 | I807 | 0 | FD CHG | 3 | 3.41 | 20.5 | 460 | 50 | 410 |
| 43 | 72 | I807 | 0 | FD CHG | 5 | 3.64 | 20.2 | 550 | 90 | 460 |
| 44 | 72 | I807 | 0 | FD CHG | 5 | 3.11 | 20.7 | 510 | 90 | 420 |
| 45 | 72 | I807 | 0 | FD CHG | 5 | 2.94 | 19.6 | 600 | 70 | 530 |
| 46 | 95 | I807 | 40 | FD CHG | 7 | 1.03 | 0.8 | 2250 | 1570 | 680 |
| 47 | 95 | I807 | 40 | FD CHG | 7 | 1.18 | 0.8 | 2310 | 1520 | 790 |
| 48 | 95 | I807 | 40 | FD CHG | 7 | 0.97 | 0.7 | 2270 | 1500 | 770 |
| 49 | 101 | I807 | 30 | FD CHG | 2 | 0.74 | 3.2 | 2320 | 1550 | 770 |
| 50 | 101 | I807 | 30 | FD CHG | 2 | 0.98 | 3.2 | 2310 | 1640 | 680 |
| 51 | 101 | I807 | 30 | FD CHG | 2 | 0.96 | 3.0 | 2300 | 1190 | 1110 |
| 52 | 39 | I807 | 0 | FD CHG | 2 | 2.58 | 32.6 | 620 | 130 | 490 |
| 53 | 39 | I807 | 0 | FD CHG | 2 | 2.44 | 35.5 | 650 | 160 | 490 |
| 54 | 39 | I807 | 0 | FD CHG | 2 | 2.82 | 32.9 | 720 | 220 | 500 |
| 55 | 96 | I807 | 0 | FD CHG | 2 | 3.98 | 33.9 | 600 | 180 | 420 |
| 56 | 96 | I807 | 0 | FD CHG | 2 | 3.92 | 40.3 | 450 | 90 | 360 |
| 57 | 96 | I807 | 0 | FD CHG | 2 | 3.00 | 31.7 | 670 | 210 | 460 |
| 58 | 109 | I807 | 30 | FD CHG | 2 | 0.76 | 10.9 | 1910 | 1230 | 680 |

TABLE 3-continued

Multilayer Assemblies Using I807 Adhesive

| Sample ID | Coat Weight (g/m$^2$) | Adhesive | % A800 (w/w) | Antimicrobial | AMX Concentration % (w/w) | PAPE T04/095 (N/25 mm) | Tack T04/001 (N/25 mm) | FHC T06/022 (g/m$^2$/24 h) | Static Absorption T06/022 (g/m$^2$/24 h) | MVTR T06/022 (g/m$^2$/24 h) |
|---|---|---|---|---|---|---|---|---|---|---|
| 59 | 109 | I807 | 30 | FD CHG | 2 | 1.71 | 9.6 | 2480 | 1850 | 630 |
| 60 | 109 | I807 | 30 | FD CHG | 2 | 1.13 | 11.3 | 2100 | 1440 | 660 |

TABLE 4

Multilayer Assemblies Using AVC-12363 Adhesive

| Sample ID | Coat Weight (g/m$^2$) | Adhesive | % A800 (w/w) | Antimicrobial | AMX Concent % (w/w) | PAPE T04/095 (N/25 mm) | Tack T04/001 (N/25 mm) | FHC T06/022 (g/m$^2$/24 h) | Static Absorption T06/022 (g/m$^2$/24 h) | MVTR T06/022 (g/m$^2$/24 h) |
|---|---|---|---|---|---|---|---|---|---|---|
| 1 | 90 | AVC-12363 | 0 | FD CHG | 9 | 5.29 | 22.5 | NT | NT | 704 |
| 2 | 90 | AVC-12363 | 0 | FD CHG | 9 | 4.95 | 21.8 | NT | NT | 768 |
| 3 | 90 | AVC-12363 | 0 | FD CHG | 9 | 5.42 | 23.2 | NT | NT | |
| 4 | 97 | AVC-12363 | 0 | FD CHG | 3 | 6.18 | 35.7 | NT | NT | 717 |
| 5 | 97 | AVC-12363 | 0 | FD CHG | 3 | 5.68 | 32.7 | NT | NT | 800 |
| 6 | 97 | AVC-12363 | 0 | FD CHG | 3 | 6.70 | 35.5 | NT | NT | 733 |
| 7 | 91 | AVC-12363 | 0 | None | 0 | 6.26 | 47.0 | NT | NT | 684 |
| 8 | 91 | AVC-12363 | 0 | None | 0 | 6.74 | 43.7 | NT | NT | 742 |
| 9 | 91 | AVC-12363 | 0 | None | 0 | 6.57 | 43.3 | NT | NT | NT |
| 10 | 106 | AVC-12363 | 20 | FD CHG | 9 | 4.39 | 17.9 | 2060 | 610 | 1450 |
| 11 | 106 | AVC-12363 | 20 | FD CHG | 9 | 4.37 | 17.6 | 1960 | 460 | 1500 |
| 12 | 106 | AVC-12363 | 20 | FD CHG | 9 | 3.61 | 17.2 | 2010 | 550 | 1460 |
| 13 | 110 | AVC-12363 | 20 | None | 0 | 3.28 | 17.0 | 1960 | 450 | 1510 |
| 14 | 110 | AVC-12363 | 20 | None | 0 | 3.18 | 16.0 | 2020 | 520 | 1500 |
| 15 | 110 | AVC-12363 | 20 | None | 0 | 2.98 | 16.2 | 2120 | 510 | 1610 |

It was determined that in all samples evaluated, the incorporation of chlorhexidine gluconate into the adhesive did not significantly impact the adhesive properties.

Evaluation of antimicrobial efficacy was also undertaken.

Antimicrobial efficacy evaluation was performed following ASTM 2180 initially on both adhesive samples with and without carboxymethyl cellulose. The rational for this choice was based upon the following. 1807 with its high concentration of —COOH functional groups might inhibit the release of the positively charged chlorhexidine gluconate. And, carboxymethyl cellulose is an anionic polymer and could retain the chlorhexidine gluconate.

Two concentration levels of chlorhexidine were tested. High levels of chlorhexidine gluconate (9% CHG into 100 gsm adhesive) were evaluated. This high concentration was chosen to evaluate whether it would be possible to achieve antimicrobial efficacy. Medium levels of chlorhexidine base were also tested (5% chlorhexidine base in 45 gsm and 100 gsm). Chlorhexidine base exhibited a low solubility in water and represented therefore a worst case.

Figure 2:
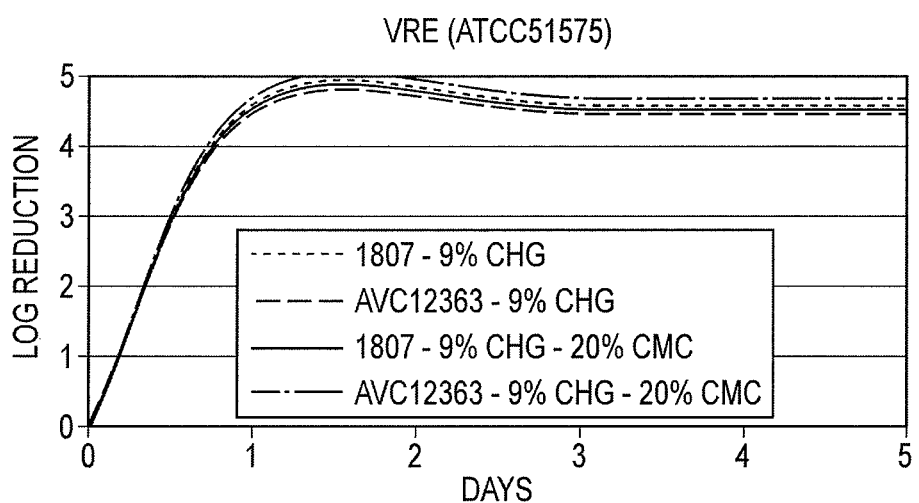
FIG. 2 is a graph illustrating antimicrobial efficacy of various adhesive samples described herein.

Antimicrobial efficacy of the various samples are illustrated in FIGS. 1 and 2. The data in the referenced figures was based upon all adhesives coated at 100 gsm. FIG. 1 represents antimicrobial efficacy following ASTM2180 without re-inoculation. FIG. 2 represents antimicrobial efficacy following ASTM2180.

In conclusion, antimicrobial efficacy of the prototypes made with 1807 or AVC-12363 with or without carboxymethyl cellulose (A800) exhibited similar antimicrobial efficacy (see FIGS. 1 and 2) at high chlorhexidine gluconate concentration. Neither the carboxymethyl cellulose nor the —COOH functional group of the 1807 adhesive appeared to inhibit the antimicrobial efficacy.

Additional details and aspects of adhesives, agents for incorporation in the adhesives, arrangements and other components for multilayer structures are provided in US 2010/0322996.

Many other benefits will no doubt become apparent from future application and development of this technology.

All patents, published applications, and articles noted herein are hereby incorporated by reference in their entirety.

It will be understood that any one or more feature or component of one embodiment described herein can be combined with one or more other features or components of another embodiment. Thus, the present invention includes any and all combinations of components or features of the embodiments described herein.

As described hereinabove, the present invention solves many problems associated with previous type products, adhesives and practices. However, it will be appreciated that various changes in the details, materials and arrangements of components and operations, which have been herein described and illustrated in order to explain the nature of the invention, may be made by those skilled in the art without departing from the principle and scope of the invention, as expressed in the appended claims.

What is claimed is:

1. An adhesive formulation including chlorhexidine, the adhesive comprising:
   an adhesive;
   at least one chlorhexidine salt; and
   an absorbent;
   wherein at least one chlorhexidine salt is soluble in the adhesive.

2. The formulation of claim 1 wherein the adhesive is selected from the group consisting of acrylic adhesives, rubber adhesives, silicone adhesives, polyurethane adhesives, and combinations thereof.

3. The formulation of claim 1 wherein the adhesive is an acrylic adhesive.

4. The formulation of claim 1 wherein the at least one chlorhexidine salt includes chlorhexidine gluconate or chlorhexidine digluconate.

5. The formulation of claim 1 wherein the chlorhexidine salt is in a powder form and is produced by an active drying operation.

6. The formulation of claim 5 wherein the active drying operation is freeze drying.

7. The formulation of claim 5 wherein the active drying operation is spray drying.

8. A medical product having an adhesive according to claim 1.

9. The medical product of claim 8 wherein the adhesive is selected from the group consisting of acrylic adhesives, rubber adhesives, silicone adhesives, polyurethane adhesives, and combinations thereof.

10. The medical product of claim 8 wherein the adhesive is an acrylic adhesive.

11. The medical product of claim 8 wherein the at least one chlorhexidine salt includes chlorhexidine gluconate or chlorhexidine digluconate.

12. The medical product of claim 8 wherein the chlorhexidine salt is in a powder form and is produced by an active drying operation.

13. The medical product of claim 12 wherein the active drying operation is freeze drying.

14. The medical product of claim 12 wherein the active drying operation is spray drying.

15. The adhesive composition of claim 1, wherein the absorbent is a hydrocolloid agent.

16. The adhesive composition of claim 15, wherein the hydrocolloid is a synthetic hydrocolloid.

17. The adhesive composition of claim 16, wherein the synthetic hydrocolloid is carboxymethyl cellulose.

18. The adhesive composition of claim 17, wherein the carboxymethyl cellulose has a particle size less than 75 μm.

19. The adhesive composition of claim 18, wherein the concentration of carboxymethyl cellulose is from about 20% to about 40% (w/w).

20. The adhesive composition of claim 19, wherein the concentration of carboxymethyl cellulose is from about 30% to about 40% (w/w).

* * * * *